(12) United States Patent
Jochum

(10) Patent No.: US 10,893,972 B2
(45) Date of Patent: Jan. 19, 2021

(54) FASTENING DEVICE OF A PENIS EXTENSION DEVICE WITH A TENSILE FORCE METER

(71) Applicant: SWISS-TEC GLOBAL LTD, Vaduz (LI)

(72) Inventor: Herbert Jochum, Feldafing (DE)

(73) Assignee: SWISS-TEC GLOBAL LIMITED, Vaduz (LI)

( * ) Notice: Subject to any disclaimer, the term of this patent is extended or adjusted under 35 U.S.C. 154(b) by 178 days.

(21) Appl. No.: 16/095,955

(22) PCT Filed: May 22, 2017

(86) PCT No.: PCT/EP2017/062301
§ 371 (c)(1),
(2) Date: Oct. 24, 2018

(87) PCT Pub. No.: WO2017/202785
PCT Pub. Date: Nov. 30, 2017

(65) Prior Publication Data
US 2019/0133809 A1    May 9, 2019

(30) Foreign Application Priority Data
May 23, 2016  (EP) .................................... 16170933

(51) Int. Cl.
*A61F 5/41* (2006.01)
(52) U.S. Cl.
CPC ........... *A61F 5/41* (2013.01); *A61F 2005/411* (2013.01); *A61F 2005/412* (2013.01)

(58) Field of Classification Search
CPC ..... A61F 5/41; A61F 2005/412; A61H 19/00; A61H 19/30; A61H 19/32
(Continued)

(56) References Cited

U.S. PATENT DOCUMENTS

| 6,162,188 A | 12/2000 | Barnea |
| 9,801,753 B2 * | 10/2017 | Jochum ..................... A61F 5/41 |
| 2010/0016759 A1 * | 1/2010 | Lavoisier ............. A61B 5/4393 |
| | | 600/587 |

FOREIGN PATENT DOCUMENTS

| CN | 105559956 A | 5/2016 |
| EP | 3463218 B1 | 7/2020 |

(Continued)

OTHER PUBLICATIONS

International Preliminary Report on Patentability in related PCT Application No. PCT/EP2017/062301, dated Nov. 27, 2018.
(Continued)

*Primary Examiner* — John P Lacyk
(74) *Attorney, Agent, or Firm* — Bacon & Thomas, PLLC

(57) ABSTRACT

A fastening device of a penis extension device includes a coupling element for exerting a tensile force on a penis and a tensile force meter, a first electronics component and a first current source. The tensile force meter electrically or electronically determines the measurement value for the exerted tension together with the first electronics component, and the first electronics component has a first radio device for transmitting the determined measurement value to an external receiver. With this device it is possible for a relevant measurement value, in particular the measurement value for the exerted tensile force, to be transmitted from the sensitive area in which the fastening device is used to an external device, for example to an app of a cell phone.

15 Claims, 9 Drawing Sheets

(58) Field of Classification Search
USPC .................................................. 600/38–41
See application file for complete search history.

(56) References Cited

FOREIGN PATENT DOCUMENTS

WO      2010000845 A1    1/2010
WO      2013041675 A2    3/2013

OTHER PUBLICATIONS

International Search Report in related PCT Application No. PCT/EP2017/062301, dated Mar. 26, 2018.
Written Opinion in related PCT Application No. PCT/EP2017/062301, dated Mar. 26, 2018.

* cited by examiner

FASTENING DEVICE OF A PENIS EXTENSION DEVICE WITH A TENSILE FORCE METER

The invention relates to a fastening device of a penis extension device with a coupling element for force transmission, to a penis extension device provided with said fastening device, and to a coupling element, according to the preambles of the independent claims.

BACKGROUND OF THE INVENTION

Penis extension appliances or devices are known in a very wide variety of designs; see, for example, DE 100 01 331 A1, U.S. Pat. No. 5,707,341 and EP 1 779 822 A1.

A portable penis extension appliance is also described in DE 10 2007 017 222 A1.

What these appliances have in common is that a long-acting tension is exerted on the penis, such that new tissue forms and leads to an enlargement of the penis. Certain diseases can also be treated using these devices. Hence, these devices are not erection aids or the like.

In the penis extension device of the kind in question here, tension is exerted on the penis in the non-erect state. For this purpose, it is necessary for the penis extension device to be connected to the penis so that this tension can be transmitted and thus exerted. It goes without saying that the starting point for transmitting the tension should be in the distal area of the fastening device. Devices serving this purpose are designated, for example, as a connecting device or fastening device. In the present document, the latter designation is used in the description of the subject matter of the invention.

Such connecting devices and fastening devices are usually provided with a coupling element, which is in turn connected to a device that exerts tension on the coupling element and then also on the fastening device and, therefore, the penis. In a simple case, the device for exerting the tension can be an elastic extension element, for example in the form of an extensible strap that is looped round the body of the user. Penis extension appliances usually have these functional parts.

To connect the penis to a penis extension device, it is known, for example, to use a loop that engages behind the glans of the penis. Condoms and cylindrical hollow bodies have furthermore been proposed (U.S. Pat. No. 5,707,341 and EP 1 779 822 A1).

So-called glans cradles are known from DE 20 206 017 667 U1 and DE 20 207 003 824 U1, onto which the penis is placed and secured with the aid of a fixing element. The fixing element engages behind the glans, and thus on the proximal side of the glans, and prevents the penis from being pulled away from the support element when tension is exerted.

The German utility model DE 202 03 927 U1 discloses a device for permanent extension of a penis. This known device is provided with a support ring suitable for bearing on the body of the user, with two parallel stretching rods which are coupled to the support ring in an articulated manner and spring-mounted in axial direction and adjustable in length, and with a fastening means mounted on the distal end of the two stretching rods for the purpose of fastening the penis. The fastening means is provided with two retention clips in the form of cylinders that are slotted in the longitudinal direction.

After the fastening means has been placed on the penis, the retention clips are latched onto the stretching rods. These stretching rods have to be pressed together telescopically beforehand or thereafter, so that they can exert a tensile force on the penis in the operational state.

WO 2013/041675 A2 (PCT/EP2012/068640) discloses a connecting device or fastening device of the type in question which is provided with an elongate, rigid hollow body, which is open at the proximal end and is used for receiving the distal end of a penis, and with an elastic sleeve for bearing on the shaft of the penis. An underpressure can be generated in the interior of the hollow body with the aid of a vacuum pump, which has the effect that the sleeve reliably seals off the interior from the shaft of the penis, specifically in such a way that the required tension is transmitted to the penis, but the sleeve and therefore the fastening device are not pulled off. The transmission of tension from the tension-exerting device to the fastening device takes place with the aid of a coupling element.

The coupling element of this known connecting device can be equipped with a tensile force meter which indicates the exerted tensile force in situ by optical means and therefore only visually.

SUMMARY OF THE INVENTION

The object of the invention is to make available a fastening device for a penis extension device, and also a penis extension device, with the aid of which it is possible for important data concerning the use of the penis extension device to be transmitted to the user in a simple and discreet manner.

This object is achieved by the teaching of the claims.

Penis extension devices usually have three elements, namely a fastening device or fixing element for a penis, a coupling element, and a device for exerting tension. The tension exerted by the latter device is transmitted to the coupling element and by this coupling element to the fastening device and, with the aid of the fastening device, to the penis that is connected thereto. The coupling element can be connected fixedly to the fastening device or can be an integral part thereof or can be releasably connectable thereto.

The subject matter of the invention is a fastening device of a penis extension device with a coupling element for exerting a tensile force on the fastening device and with a tensile force meter. With the aid of the coupling element, a force, namely a tensile force, is transmitted to the fastening device and from there to the penis. The extension treatment described above can be carried out by means of this transmission of force or transmission of tension.

The device that exerts a force (more precisely tension) on the coupling element engages on the coupling element. In the context of the present document, this device is also designated as a device for exerting tension. It can be a classical extension element of the type described above. However, the invention is not limited to such an extension element. Instead, it is possible to use any device of a known type that is known in the prior art and is suitable for this purpose.

This device for exerting tension can also be of the kind in the aforementioned DE 202023927 U1.

The fastening device is now characterized in that a first electronics component and a first current source are present. Moreover, the tensile force meter electrically or electronically determines the measurement value for the exerted tension together with the first electronics component. Furthermore, the first electronics component has a first radio device for transmitting the determined measurement value to an external receiver. The first current source supplies this radio device and this electronics component with the required energy.

With this fastening device according to the invention, it is possible for a relevant measurement value, in particular the measurement value for the exerted tensile force, to be transmitted from the sensitive area in which the fastening device according to the invention is used to an external device, for example to an app of a cell phone. The cell phone can be privately checked or read, respectively, by the user.

From this app, the user can see the strength of the tensile force exerted in the past or of the tensile force currently exerted. These values can also be integrated over time.

Thus, the person wearing the fastening device according to the invention, or wearing a penis extension device equipped with the latter, has external access to information and is able to take the necessary measures. For example, the user can establish whether too much tensile force or too little tensile force was exerted in the last relevant time period. Values of this kind can be stored and/or processed in the element in which, for example, the electronics component is arranged. To this end, a chip or the like suitable for this purpose has to be present. However, this storing and/or processing can also take place in an external unit which receives the data transmitted from the receiver, for example in a cell phone.

The tensile force meter preferably comprises a strain gauge or a distance measurement device.

A strain gauge can, for example, be adhesively bonded to a beam or a flexural beam. In the latter case, the flexural beam bends in proportion to the exerted force and causes a change of resistance in the strain gauge. Such strain gauges are in the form of a Wheatstone full bridge of half bridge and deliver an output signal (difference sign) proportional to the exerted force.

The first electronics component, with a Bluetooth module as interface to the outside, supplies the Wheatstone bridge with a stabilized direct voltage and amplifies the "small" output signal. The energy supply is effected with the aid of the first current source, for example with a battery or an accumulator.

It is also possible, alternatively and preferably, to use a distance measurement device, which can preferably be an inductive, resistive or capacitive distance measurement device.

It is particularly preferably a Hall effect sensor, which is connected by a cable to the first electronics component, the latter being equipped with said Bluetooth module. Further configurations of a Hall effect sensor of this kind are found below and in particular in the description of the figures.

The coupling element can be a component part of the fastening device. Preferably, however, the coupling element is a separate element which is suitable for being connected to the fastening device and also for being released from the latter again. To put it another way, the coupling element can be connected to the fastening device and can also be released again therefrom.

It is also preferable that the coupling element is articulated on the fastening device so as to be pivotable about at least one axis.

The first radio device is preferably a Bluetooth device.

It is also preferable that the tensile force meter, the first electronics component and/or the first current source are integrated in the coupling element. It is thus also possible for these elements to be distributed both in the fastening device and also in the coupling element.

It goes without saying that all the elements needed for a correct function of the tensile force meter are covered by the expressions "electronics component" and "tensile force meter" used here, without these parts or elements being explicitly mentioned, for example wiring and individual parts of the measurement device.

According to a preferred first variant, the fastening device according to the invention has an elongate, rigid hollow body which is open at the proximal end and which is suitable for receiving the distal end of the penis and for fastening to the penis extension device. This hollow body has an opening which is operatively connected to a vacuum pump or can be brought into such operative connection or is suitable for being brought into such operative connection. This opening is preferably formed at the distal end of the hollow body. This fastening device is moreover equipped with an elastic tubular sleeve for bearing with its proximal area on the shaft of the penis and, in the assembled state of the fastening device, for having its distal area enclosing the proximal end of the hollow body and bearing on the outside thereof. In other words, this sleeve is suitable for being placed with its proximal area on the shaft of the penis and, in the assembled state of the fastening device, for enclosing with its distal area the proximal end of the hollow body.

A fastening device with the last-mentioned features is also known from WO2013/041675 A2 (PCT/EP2012/068640) already mentioned in the introduction, the disclosure of which is herewith referred to and incorporated into the present documentation.

This fastening device according to the first variant is characterized in that a pressure meter is present for determining the pressure prevailing inside the hollow body, and either i) the pressure meter electrically or electronically determines the pressure measurement value together with the first electronics component, and the first radio device of the first electronics component is suitable for transmitting the determined pressure measurement value to an external receiver, or ii) a second electronics component and a second current source are present, the pressure meter electrically or electronically determines the measurement value for the pressure together with the second electronics component, and the second electronics component has a second radio device for transmitting the determined measurement value to an external receiver.

In this first variant, therefore, a pressure meter is also present in addition to a tensile force meter. These devices can be equipped with separate electronics components, namely a first and a second electronics component, with separate current or energy sources, namely a first and a second source, and also with separate radio devices, namely a first and a second radio device.

However, it is also possible that both devices jointly use a current source, an electronics component and/or a radio device.

According to a second variant, the subject matter of the invention is moreover a fastening device of a penis extension device with a coupling element for force transmission, wherein the fastening device has an elongate, rigid hollow body which is open at the proximal end and which is suitable for receiving the distal end of the penis and for fastening to the penis extension device and has an opening which is preferably arranged at its distal end and which is operatively connected to a vacuum pump or is suitable for being brought into such operative connection, and an elastic tubular sleeve for bearing with its proximal area on the shaft of the penis and, in the assembled state of the fastening device, for having its distal area enclosing the proximal end of the hollow body and bearing on the outside thereof.

A fastening device of this kind is likewise described in the aforementioned WO2013/041675 A2 (PCT/EP2012/068640).

This fastening device according to the second variant is characterized in that a pressure meter is present for determining the pressure prevailing inside the hollow body, the pressure meter electrically or electronically determines the pressure measurement value together with a first electronics component, and the first electronics component has a first radio device for transmitting the determined pressure measurement value to an external receiver.

In the second variant of the fastening device according to the invention, a measurement value is likewise transmitted to the outside from the sensitive area. Thus, with the aid of an app as described above, a user can establish whether the underpressure prevailing inside the hollow body is sufficient to prevent a situation where, for example, the fastening device, in particular the sleeve, is pulled off or slips off the penis. If the internal pressure exceeds a defined value, such that a sufficient vacuum or a sufficient underpressure is no longer present, it is possible, for example, for an alarm to be communicated to the user with the aid of the app.

It is furthermore preferable, in the first variant and the second variant, that a three-way valve is arranged between the opening and the vacuum pump and can adopt the following settings:
i) the interior of the hollow body is connected to the environment,
ii) the opening and therefore the hollow body are closed, and
iii) the interior of the hollow body is connected to the vacuum pump.

This fastening device can be equipped with a tensile force meter in which the exerted tension is indicated by optical means. A tensile force meter of this kind can likewise be used in the fastening device according to the invention, but only in addition to the electronic or electrical tensile force meter and/or pressure meter according to the invention.

According to a further preferred embodiment, the fastening device having the above-described features, together with the coupling element having the likewise above-described features, is integrated in a penis extension device. The subject matter of the invention is therefore a penis extension device which comprises a fastening device, a tension-exerting device, and a coupling element for transmitting force from the tension-exerting device to the fastening device, and also a tensile force meter.

This penis extension device has a first electronics component and a first current source with the above-described feature(s). The tensile force meter electrically or electronically determines the measurement value of the exerted pressure together with the first electronics component. The first electronics component has a first radio device for transmitting the determine measurement value to an external receiver.

The tensile force meter of this penis extension device preferably has a strain gauge or a distance measurement device of the type described above and/or the first radio device is a Bluetooth device.

This penis extension device can be one with a support ring suitable for bearing on the body of the user, with two longitudinally adjustable stretching rods which are articulated in parallel on the support ring and are axially resiliently mounted, with a fastening device arranged at the distal end of the two stretching rods and suitable for fastening the penis, and with a coupling element for force transmission.

A penis extension device having the last-mentioned features is known from the utility model DE 202 03 927 U1 already discussed in the introduction, the disclosure of which is herewith referred to and incorporated into the present documentation.

The latter penis extension device is characterized in that the first electronics component, the first current source and the tensile force meter are arranged in one of the two stretching rods, in both stretching rods or in the coupling element. Said elements can be distributed in any desired manner.

The coupling element is in this case preferably suitable for being connected to the two stretching rods and also for being released from the latter again.

The subject matter of the invention is moreover a coupling element for a penis extension device, which coupling element is suitable for transmitting a tensile force to a fastening device for a penis, wherein the coupling element is an element separate from the fastening device and is suitable for being connected to the fastening device, and also for being released from the latter again. The coupling element can therefore be connected to the fastening device and can be released from the latter again.

This coupling element is characterized in that a first electronics component, a first current source and a tensile force meter, which electrically or electronically determines the measurement value for the exerted pull together with the electronics component, are integrated in the coupling element, and in that the first electronics component has a radio device for transmitting the determined measurement value to an external receiver.

BRIEF DESCRIPTION OF THE DRAWINGS

The invention is explained in more detail below with reference to the attached drawings, in which.

DETAILED DESCRIPTION OF THE INVENTION

Figure 1:
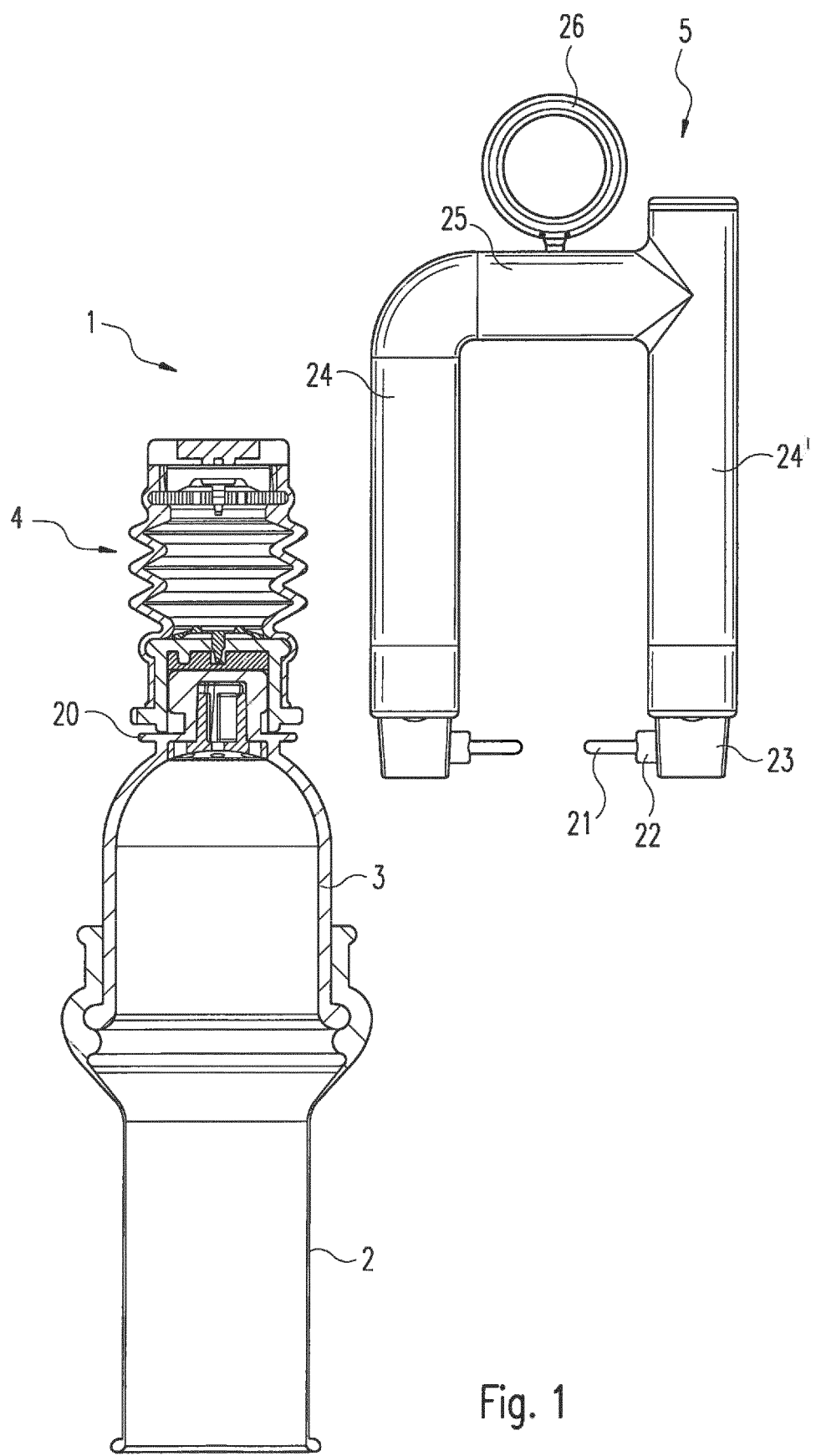
FIG. 1 shows a fastening device in cross section and a coupling element in a side view, wherein fastening device and coupling element are shown in the separated state.

FIG. 1 shows a fastening device 1 according to the invention, partially in sectional view and partially in side view, which is equipped with a sleeve 2 made of medical silicone, which sleeve 2 is connected to a rigid hollow body 3, which in turn is connected to a vacuum pump 4.

This fastening device 1 moreover comprises a coupling element 5 which can be pivotably connected to the hollow body 3 or the fastening device 1 and is releasable again. In FIG. 1, the coupling element 5 is shown separate from or released from the fastening device 1. The fastening device corresponds to the aforementioned first variant on its own, i.e. without coupling element, and is described in detail in WO2013/041675 A2 (PCT/EP2012/068640).

To connect the fastening device 1 (more precisely the hollow body 3) to the coupling element 5, an outwardly radially peripheral collar 20 is provided at the distal end of the hollow body 3, and a ring 21 engages behind said collar 20. This ring 21 is not closed but open, such that can be fitted laterally with elastic expansion onto the hollow body 3 and can engage behind said collar 20.

Figure 2:
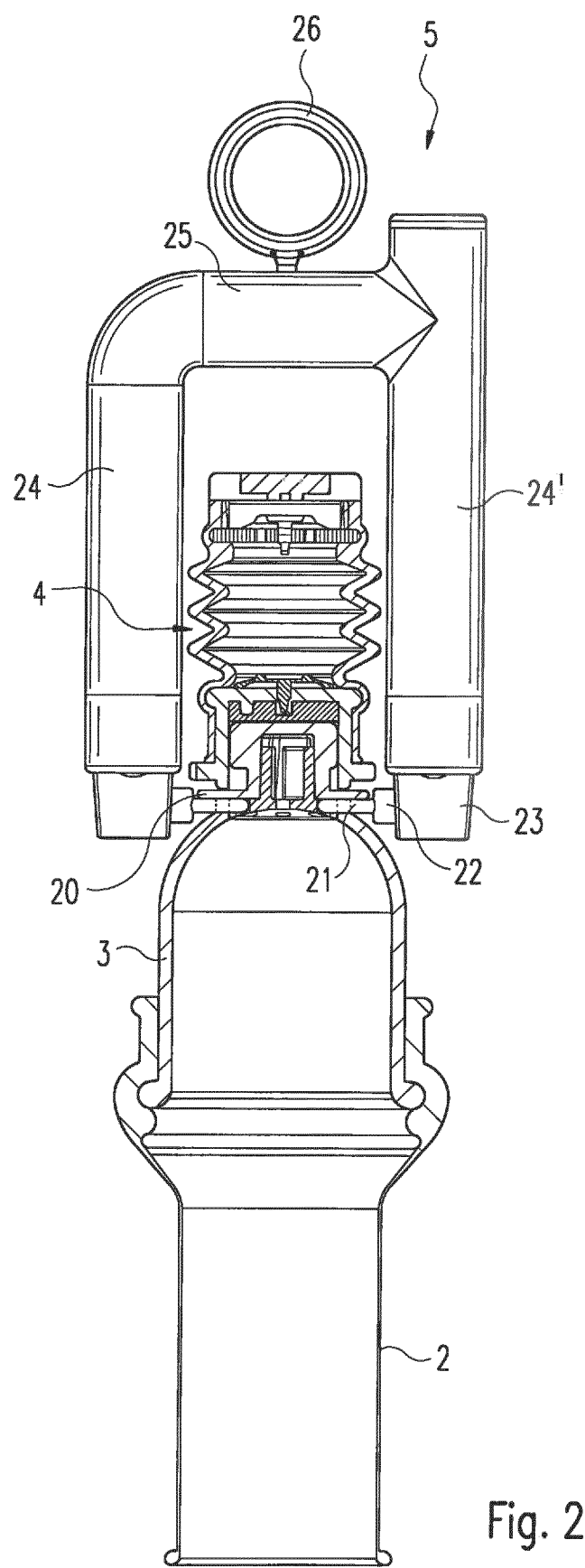
FIG. 2 shows a view analogous to FIG. 1, but with fastening device and coupling element in the assembled state.

This assembled state, in which the fastening device 1 is connected to the coupling element 5, is shown in FIG. 2.

Figure 3:
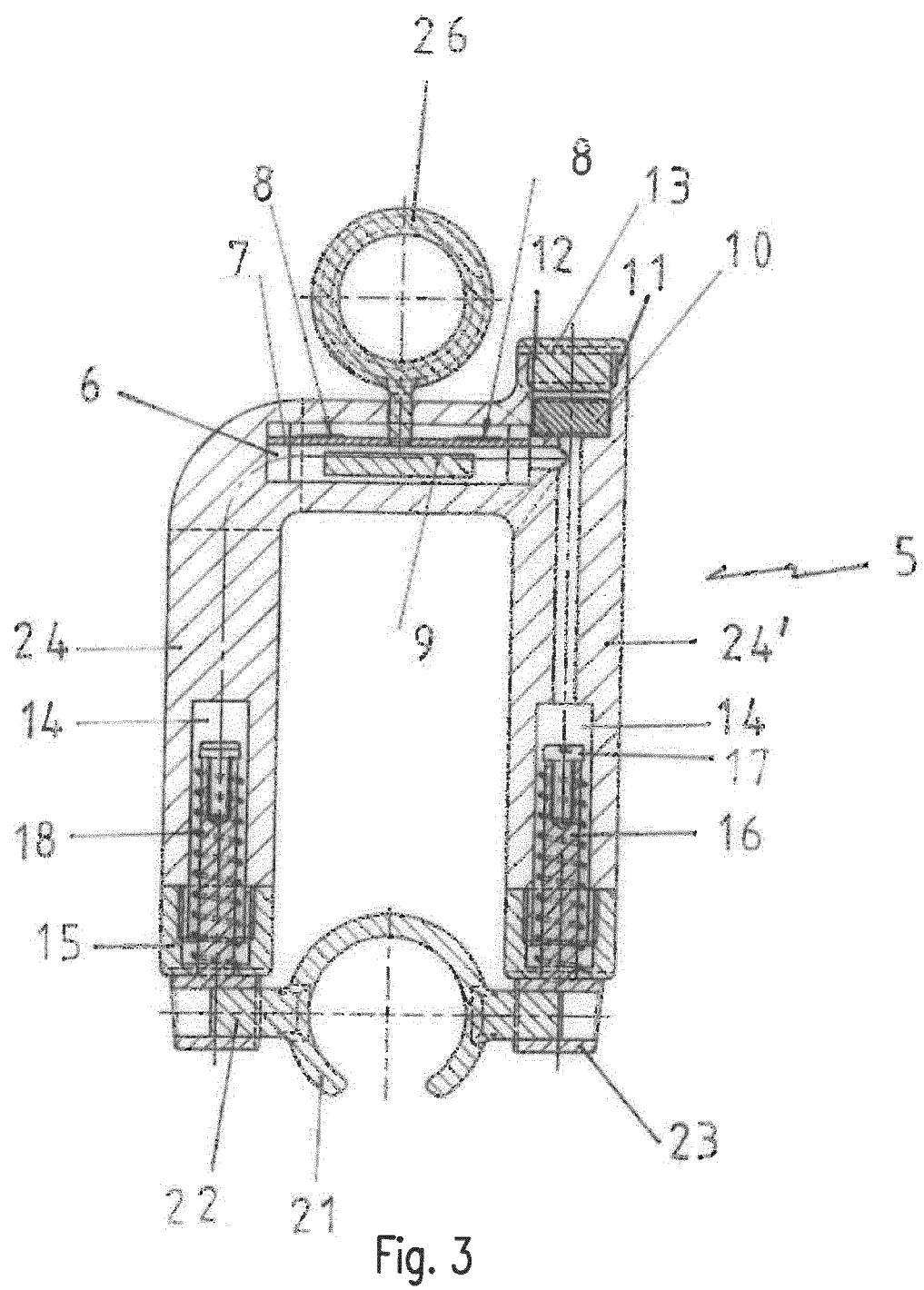
FIG. 3 shows a sectional view through a coupling element for a fastening device according to a first embodiment.

The ring 21 is mounted on the coupling element 5 and is provided with two radially extending pegs 22 which, lying diametrically opposite each other, are connected to the ring 21 or integrally formed thereon (see also FIG. 3). These pegs 22 extend radially outward and thus perpendicularly with respect to the longitudinal axis of the fastening device 1.

A bearing bushing 23 of the coupling element 5 can be pushed respectively onto the two pegs 22. The pegs 22 protrude into the associated interior of the bearing bushing 23 and provide for rotary mounting of the coupling element 5.

The coupling element 5 is equipped with two bow arms 24, 24' which extend approximately parallel and which are connected at their distal end by an arch 25.

This results in an approximately U-shaped element, which is pivotable.

At the distal end of the coupling element 5, a fixture 26 is present on the arch 25 and, in the embodiment shown, is in the from of a ring, by means of which a connection can be made to the tension-exerting device of the penis extension device.

At their free ends toward the ring 21, the bow arms 24, 24' each have an outwardly open cavity 14. Caps 15 are screwed respectively onto the free ends of these hollow bow arms 24, 24', which caps 15 close off the hollow bow arms 24, 24'. The caps 15 are provided with a central bore through which a hollow cylindrical pin 16 in each case extends inward from the outside. At its free lower end, the hollow cylindrical pin 16 is connected to the bearing bushing 23. A threaded screw 17 and a helical spring 18 are in each case arranged in the interior of the bow arms 24, 24' and thus in the cavities 14. The threaded pin of the threaded screw 17 protrudes into the spring 18; one side of the spring 18 bears on the head of the threaded screw 17, while the other side of the spring 18 is supported on the bottom of the cap 15. In their bottom, the caps 15 each have a bore through which the hollow cylindrical pin 16 extends from the outside into the spring 18.

The threaded pin of the threaded screw 17 is screwed into the associated hollow cylindrical pin 16, which for this purpose has a corresponding thread.

In the assembled state, the hollow cylindrical pin 16 protrudes into the associated bow arm 24, 24' and is not visible from the outside. In other words, the bearing bushing 23 lies on the free end of the bow arm 24, 24'. When a tensile force is exerted on the coupling element, the hollow cylindrical pin 16 is pulled to a greater or lesser extent out of the bow arm 24, 24'. A marking 19, which has three areas of different colors, is located on the outside of the hollow cylindrical pin 16. The greater the tensile force exerted, the farther the hollow cylindrical pin 16 is pulled out of the bow arm 24, 24' counter to the force of the spring 18. The more the hollow cylindrical pin 16 is pulled out, the more of the marking 19 is also visible from the outside. In this way, the tensile force exerted is indicated visually.

In this embodiment shown, this visual indication of the tensile force is therefore present in addition to the electronic tensile force meter.

A coupling element of this kind with the last-mentioned features is likewise described in detail in WO2013/041675 A2 (PCT/EP2012/068640).

The coupling element according to the invention now has the features described in detail below.

A cavity 6 is provided in the interior of the arch 25. This can be seen in particular from FIG. 3.

A deformation body 7, which is connected to the fixture or the ring 26, is arranged in the cavity 6. This deformation body 7 is a flexural beam, which is adhesively bonded to a strain gauge 8. The deformation body 7 or the flexural beam bends proportionally to the exerted force and causes a change of resistance in the strain gauge 8.

The strain gauges 8 are connected in the form of a Wheatstone full bridge and deliver an output signal or difference signal proportional to the exerted force.

Also arranged in the interior 6 is a first electronics component 9 which supplies the Wheatstone bridge with a stabilized direct voltage and amplifies the small output signal.

A first current source 10 in the form of a battery is present for supplying energy.

The bow arm 24' shown on the right in FIG. 3 extends past the arch 25 and forms a kind of continuation 11 into which a bore 12 extends from the outside and from above. The first current source 10 is inserted into this bore 12. The opening of the bore 12 is closed by a screw-on lid 13.

This bore 12 merges into a bore 48 of smaller diameter, which extends as far as the cavity 14.

Figure 4:
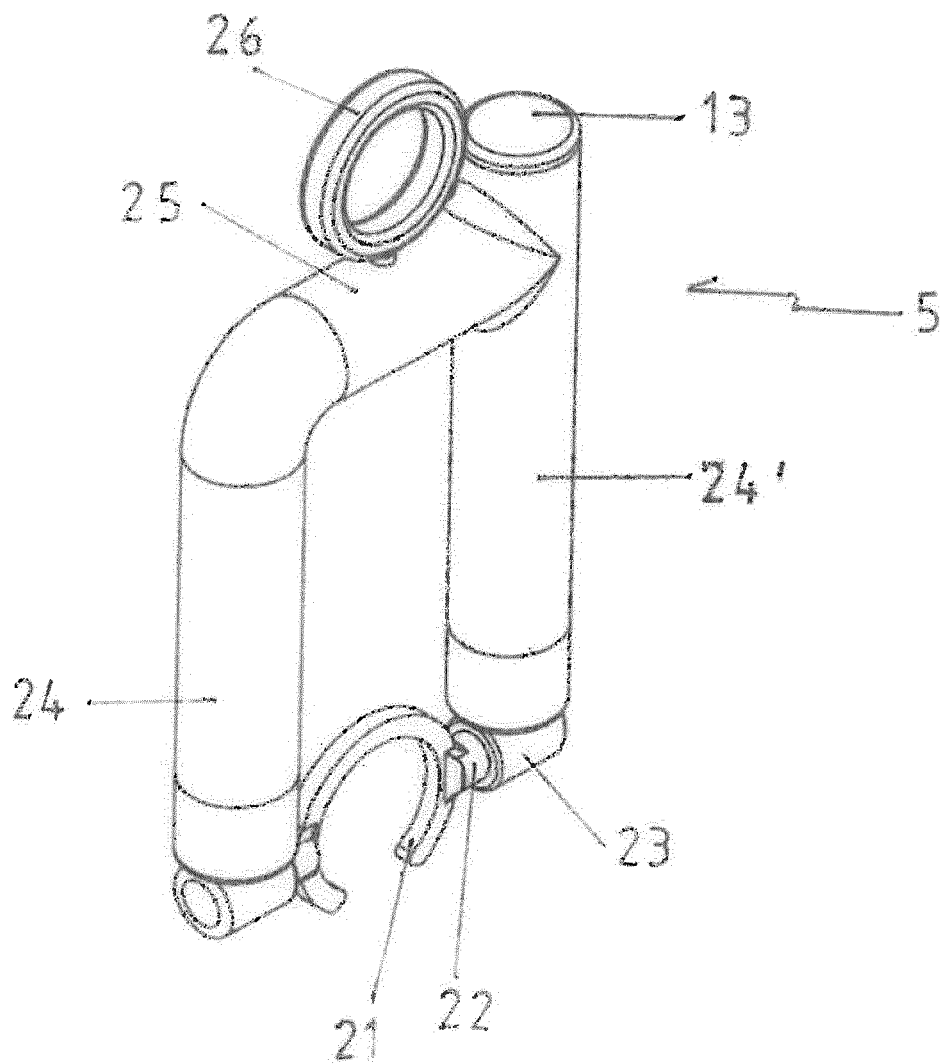
FIG. 4 shows a perspective view of the coupling element shown in FIG. 3 and in FIG. 5.
Figure 5:
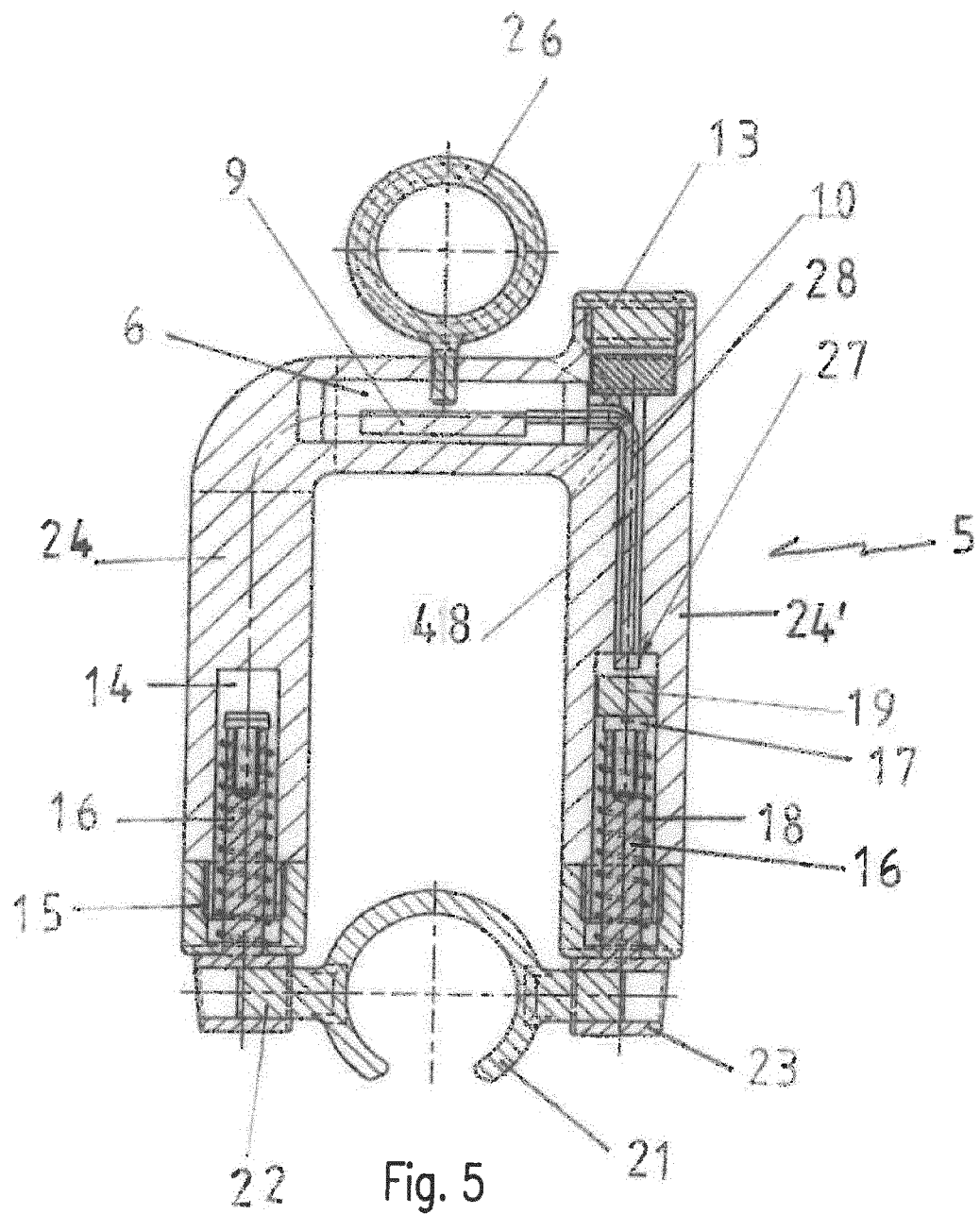
FIG. 5 shows a second embodiment of a coupling element for a fastening device according to the first embodiment.

FIG. 5 also shows a coupling element 5 in sectional view. Elements that are also present in the coupling element 5 according to FIGS. 3 and 4 are labeled with the same reference signs. The perspective view corresponds to the view shown in FIG. 4.

The difference between the coupling element 5 according to FIG. 3 and the coupling element according to FIG. 5 is that different tension meters are used.

In the embodiment shown in FIG. 5, a distance measurement device with a Hall effect sensor 27 is used, which is connected by a cable 28 to the first electronics component 9. The cable 28 extends through the bore 48 from the Hall effect sensor 19 to just before the first current source 10 and then extends through a branch bore, which connects the hollow bore 6 to the bore 48, as far as the first electronics component 9.

The coupling element 5 of this embodiment is similar to the coupling element 5 of FIG. 3 in terms of the bow arms 24, 24'.

A hollow cylindrical pin 16 is inserted respectively in the open cavities 14. Moreover, a threaded screw 17 and a spring 18 are arranged in each case in the cavities 14. The threaded pin of the threaded screw 17 in each case protrudes into the spring 18.

A magnet 19 is mounted on the head of one of the threaded pins 17 and connected thereto. The Hall effect sensor 27 measures the distance from the magnet 19 and thus delivers a distance signal. When the spring characteristic is known, the force can be easily calculated. A first battery 10 serves to supply energy.

The magnet 19 can also be a cylindrical sleeve which is arranged between the threaded screw 17 and the hollow cylindrical pin 16 and through which the threaded screw 17 extends into the hollow cylindrical pin 16 and fixes the cylindrical sleeve by means of its head. This arrangement (not shown in the figures) of threaded screw, magnetic cylindrical sleeve and hollow cylindrical pin corresponds approximately to the arrangement, explained in detail below, of said elements or parts in the inductive distance measurement device.

Figure 10:
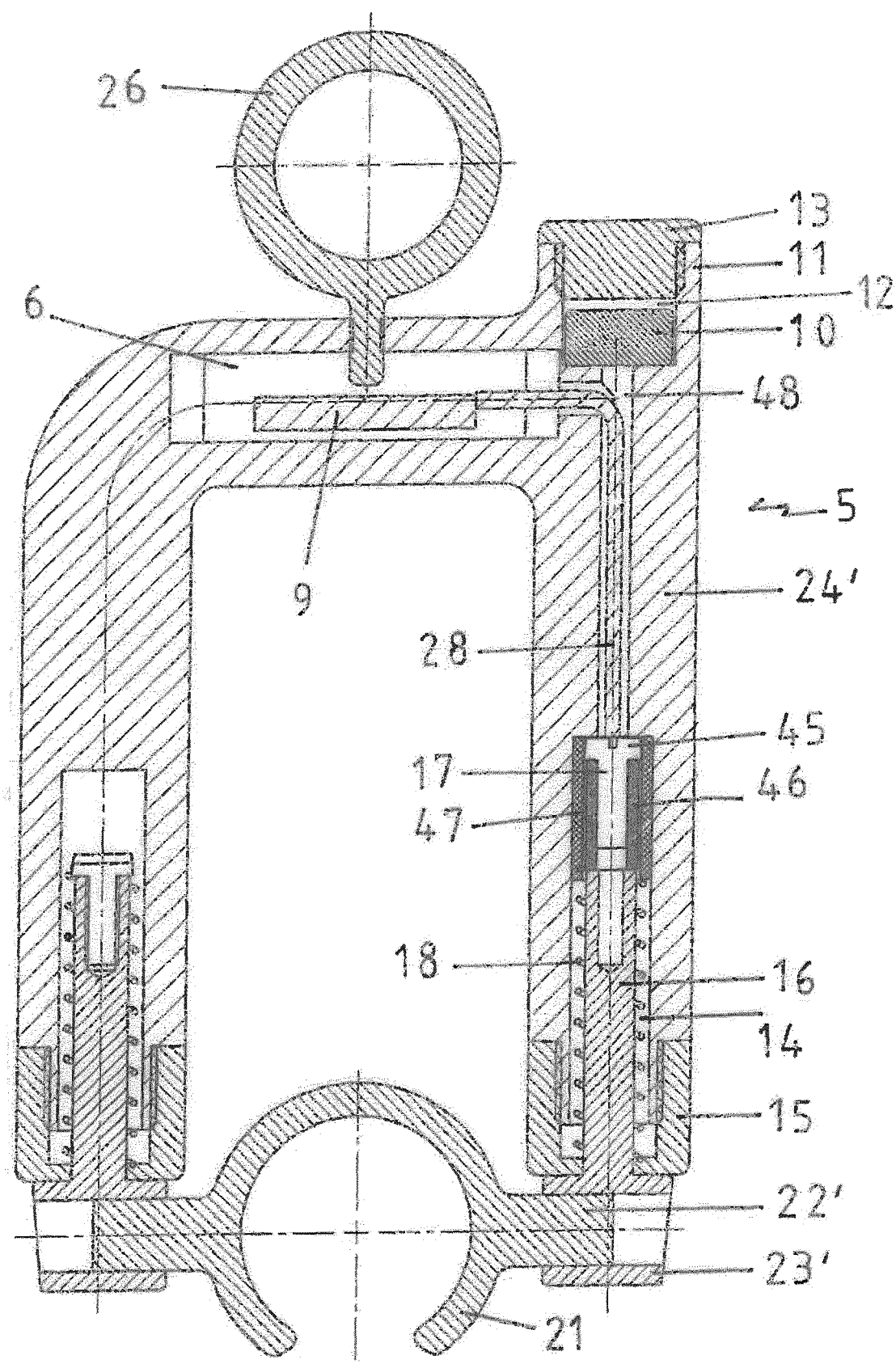
FIG. 10 shows a sectional view, corresponding to FIGS. 3 and 5, of a third embodiment of a coupling element for a fastening device according to the first embodiment.

A further embodiment of the coupling element 5 is shown in FIG. 10. This embodiment largely corresponds to the embodiment according to FIG. 5. The difference is that the distance measurement device with a Hall effect sensor according to FIG. 5 is replaced by an inductive distance measurement device. Therefore, only this difference of the inductive embodiment is described below; the other elements correspond to those of the embodiment according to FIG. 5 and are also provided with the same reference signs.

In this inductive embodiment too, a threaded screw 17 is provided in the cavity 14 of the bow arm 24', which threaded screw 17 extends into the hollow cylindrical pin 16 and is screwed into the latter. However, the approximately cylindrical head 45 of the threaded screw 17 is spaced apart from the free edge of the hollow cylindrical pin 16. In the space between the free edge of the hollow cylindrical pin 16 and the head 45 of the threaded screw 17 there is a cylindrical sleeve 46, which is held in position between this head 45 and the free edge of the hollow cylindrical pin 16 by the threaded screw 17 extending through this cylindrical sleeve 46.

The external diameter of the hollow cylindrical pin 16 corresponds approximately to the external diameter of the cylindrical sleeve 46 and of the head 45.

The cylindrical sleeve 46 is made of a soft magnetic material or contains such a material, for example ferrite, iron.

Moreover, a cylindrical coil 47 or a coil system is inserted in the cavity 14 of the bow arm 24', is fixed in position, and extends about the cylindrical sleeve 46 at a short radially outward distance.

When a tensile force is exerted on the coupling element 5, the cylindrical sleeve is moved with respect to the cylindrical coil 47. In this way, a change of inductance occurs which is measurable and represents a measure of the tensile force exerted. The electronics needed for this are known and are therefore not explained in more detail. These electronics have to be integrated in the coupling element 5 of course, for example in the electronics component 9.

In all the embodiments or coupling elements 5 according to FIGS. 3, 5 and 10, the first electronics component 9 is provided with a Bluetooth module as interface to the outside. The relevant data are transferred outward via this interface, for example to an app of a cellphone by radio. This Bluetooth module thus represents the radio device.

The fastening device 1 shown in FIGS. 1 and 2 not only has a hollow body 3 and a sleeve 2, but also a vacuum pump 4. The design of this vacuum pump 4 is of a known type and is described in the document WO2013/041675 A2 (PCT/EP2012/068640) already discussed above. Reference is herewith made once again to the disclosure of said document. Therefore, details concerning the specific structure of the vacuum pump 4 are not needed.

By actuation of this vacuum pump 4, an underpressure can be generated in the interior of the hollow body 3, with the result that the sleeve 2 bears sealingly and with force-fit engagement on the shaft of the penis.

A pressure meter can be arranged in the wall of the hollow body 3. The first electronics component 9, the first current source 10 and the radio device can be arranged in the coupling element 5 in the manner described above. The electrical contact can be ensured by means of a cable between the pressure meter and the electronics component.

Figure 6:
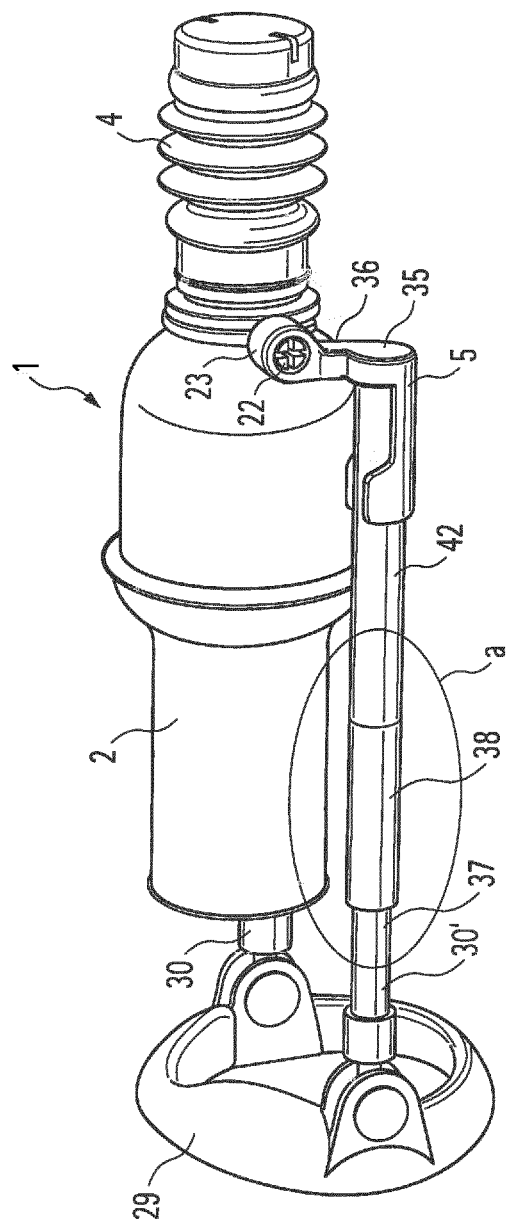
FIG. 6 shows a perspective view of a penis extension device with a support ring and, fastened thereon in an articulated manner, stretching rods, which is connected via a further embodiment of a coupling element to a fastening device according to FIGS. 1 and 2.

FIG. 6 shows a perspective view of a penis extension device with a support ring 29 which can be supported on the body of the user, and two stretching rods 30, 30' which are mounted pivotably on the front thereof and are mounted in an axially resilient manner. An arrangement of this kind is known from the aforementioned DE20203927 U1.

At the distal end of the two stretching rods 30, 30', a coupling element 5 is present which connects the two stretching rods 30, 30' to a fastening device 1 according to FIGS. 1 and 2.

The latter fastening device 1 has a hollow body 3, a sleeve 2 and a vacuum pump 4 of the kind described in connection with FIGS. 1 and 2.

Figure 8:
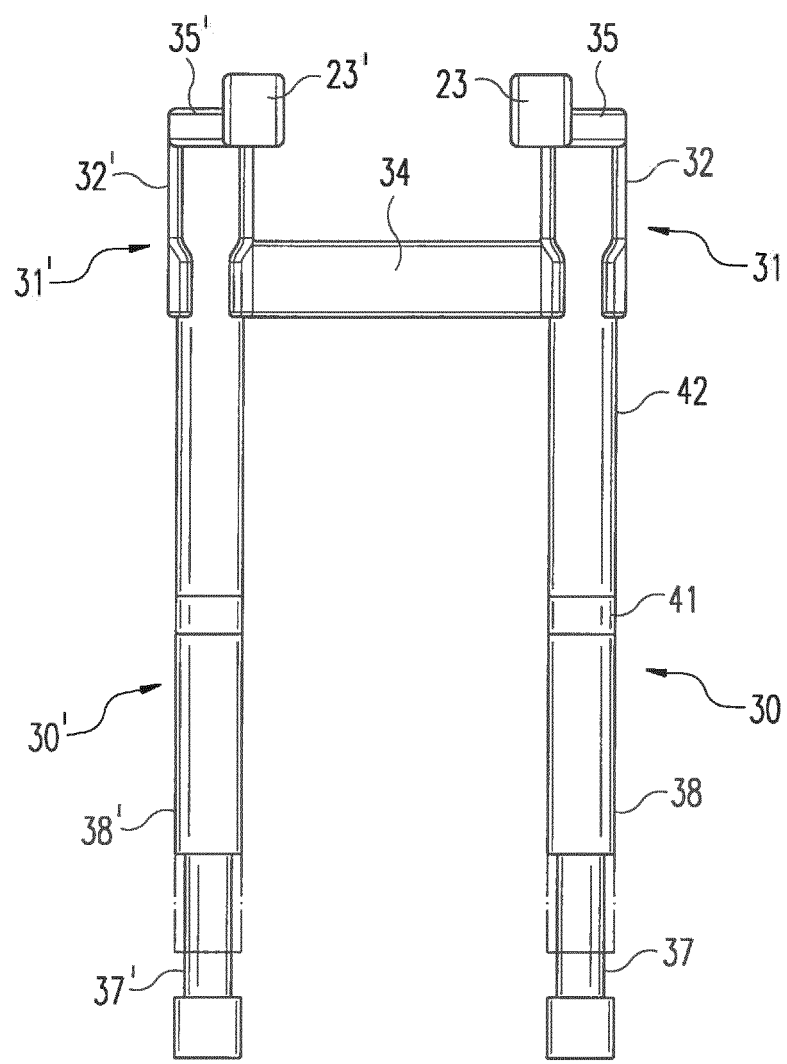
FIG. 8 shows a plan view of the two stretching rods of the penis extension device according to FIG. 6, with the coupling element which is also shown in FIG. 6.
Figure 9:
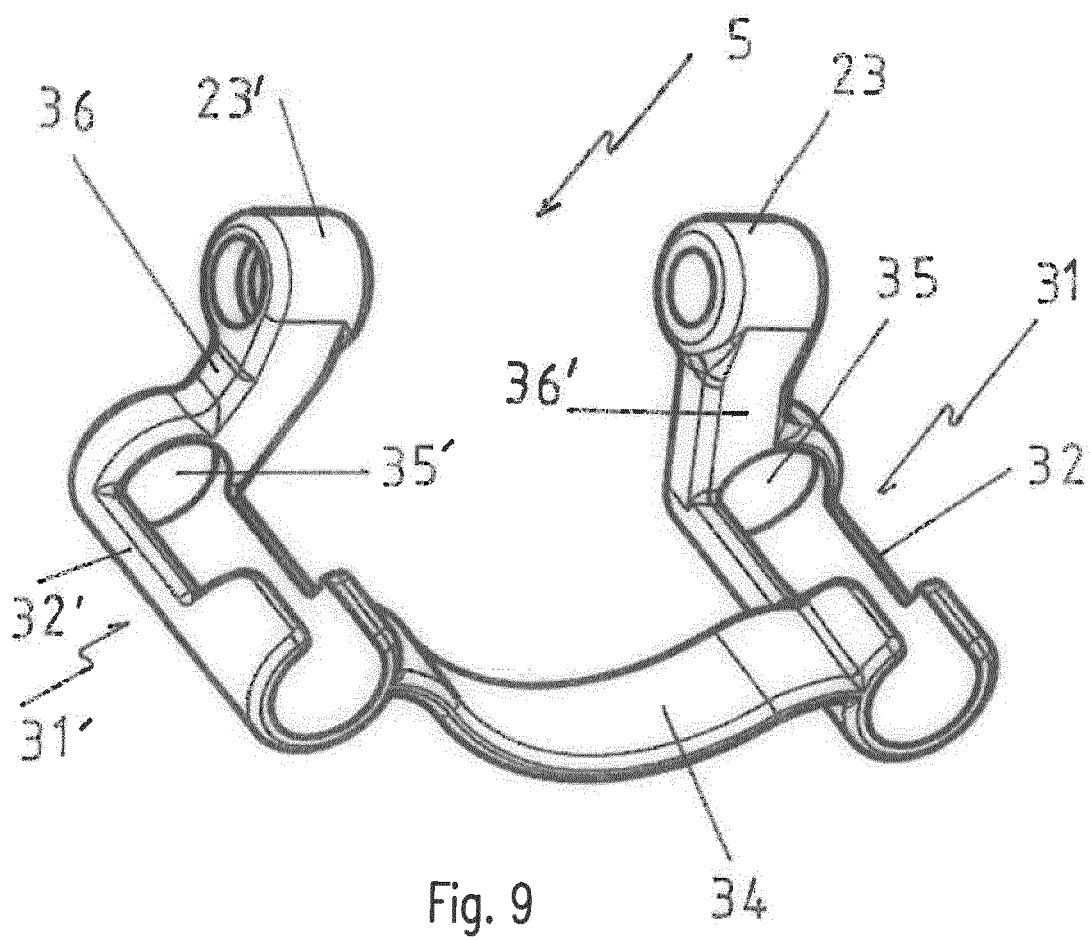
FIG. 9 shows a perspective view of the coupling element shown in FIGS. 6 and 8.

As can be seen in particular from FIG. 8, the coupling element 5 has two retention clips 31, 31' which each have longitudinally slotted hollow cylinders with resilient cheeks that can be applied to the stretching rods 30, 30' from the sides. These hollow cylinders 32, 32' are closed at their distal end.

The hollow cylinders 32, 32' can be pushed onto the stretching rods 30, 30' not only from the side, but also in the axial direction.

In the assembled state, a retention clip 31, 31' thus sits respectively on the distal end of the associated stretching rod 30, 30'.

The two retention clips 31, 31' are rigidly connected to each other by means of a band-like connection element 34 which is arranged on the proximal ends and thus on the ends of the hollow cylinders 32, 32' facing toward the support ring 29.

The connection element 34 has a bulged shape, such that it forms a kind of segment of a circle.

A connection web 36, 36' is integrally formed on the distal end of the two retention clips 31, 31', which are each closed by a lid 35, 35', and the free end of the connection web 36, 36' is designed as a bearing bushing 23, 23' in which a peg 22, 22' comes to lie in the assembled state. These pegs 22, 22' are connected to the fastening device 1. In this way, a connection of the fastening device 1 to the coupling element 5 is achieved that is pivotable about the longitudinal axis of the pegs 22, 22'.

The sleeve 2 serves to attach the fastening device 1 to the penis.

The two stretching rods 30, 30' each have a proximal rod portion 37, 37' and a distal rod portion 38, 38'. The distal rod portions 38, 38' are, at least in some areas, hollow rods into which the proximal rod portions 37, 37' can be pushed like a telescope.

A threaded screw 39 is screwed into the distal end of the two proximal rod portions 37, 37'. A compression spring 40, which extends through the interior of the distal rod portion 38, is supported on the head 43 of the threaded screw 39.

On the jacket surface, the distal end of the distal rod portion 38 has a thread 33 in which a threaded pin 41 is screwed. This threaded pin 41 is connected to the end portion 42 of the stretching rod 30.

When the proximal end portion 37 is pushed into the distal rod portion 38 in the manner of a telescope, the spring 40 is then compressed. The spring 40 releases a force in the direction of the coupling element 5.

The end portion 42 can be divided into several areas, which can be screwed onto each other. In this way, the length of the stretching rods 30, 30' can be varied.

In one of the stretching rods 30, 30', a Hall effect sensor 27 is mounted on the threaded pin 41, while a magnet 19 is arranged on the head 43 of the threaded screw 39. This magnet 19 is a cylindrical ring through which the threaded screw 39 extends.

When the position of the proximal rod portion 37 relative to the distal rod portion 38 changes, the distance from the magnet 19 to the Hall effect sensor 27 changes. The Hall effect sensor 27 thus measures the distance to the magnet 19. The mechanism here is the same as the one described above.

Figure 7:
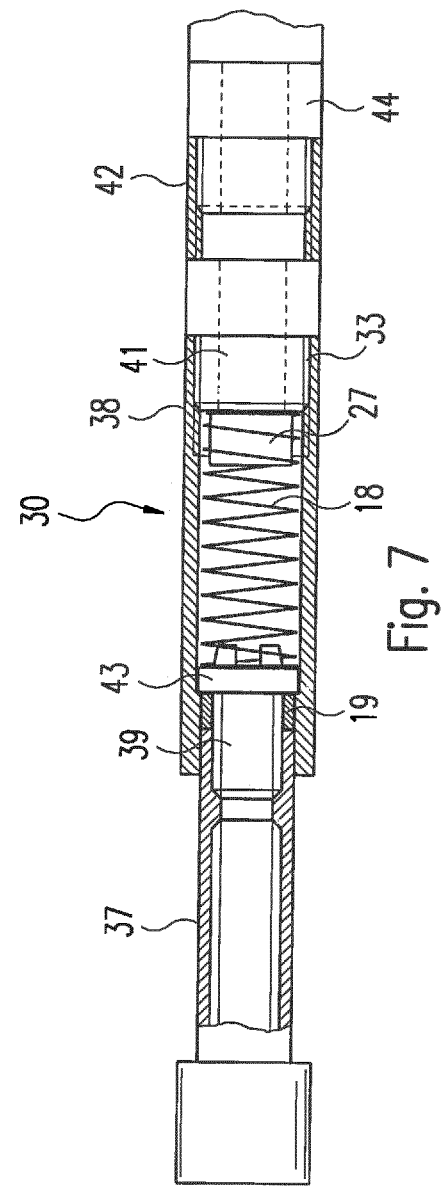
FIG. 7 shows a sectional view of the detail a from FIG. 6.

The end portion 42 of the stretching rod 30 in which the Hall effect sensor 27 and the magnet 19 are accommodated is inwardly hollow, such that the other necessary components can be accommodated in its interior. These include the first electronics component, the first current source, the cabling and the first radio device. These elements or parts are not shown in FIG. 7.

The free end of this "inwardly hollow" end portion 42 is or can be closed by a lid 44 in the form of a threaded screw that seals off this cavity from the outside.

Instead of a distance measurement device with a Hall effect sensor, it is also possible to use an inductive distance measurement device of the type described above (not shown).

To apply the penis extension device according to FIG. 6, the user guides his penis through the support ring 29 and into the sleeve 2 of the fastening device, which is not yet connected to the stretching rods 30, 30'.

The user then presses the two stretching rods 30, 30' together and connects these stretching rods to the coupling element 5 in which, for example, the two ends of the stretching rods 30, 30' are clipped into the retention clips 31, 31'.

After it has been released, the spring 18 of each stretching rod 30, 30' exerts a force in the direction of the distal end of the stretching rods 30, 30'. This force is transmitted to the penis in the form of a tensile force by means of the coupling element 5 and of the fastening device 1 and also by means of the sleeve 2.

The strength of this tensile force can be determined with the aid of the described distance measurement devices and the parts or elements interacting therewith and can be transferred to an app via the radio device.

Most parts or elements of the fastening device according to the invention can be made of plastic. They are, in particular, plastic injection-molded parts. Of course, this applies only insofar as it is technically feasible and/or unless indicated otherwise in the document. Stretching rods, springs and threaded screws are expediently made of metal.

LIST OF REFERENCE SIGNS 1 fastening device
2 sleeve
3 hollow body
4 vacuum pump
5 coupling element
6 cavity
7 deformation body
8 strain gauge
9 first electronics component
10 first current source
11 continuation
12 bore
13 screw-on lid
14 cavity
15 caps
16 hollow cylindrical pins
17 threaded screws
18 spring
19 magnet
20 collar
21 ring
22, 22' peg
23, 23' bearing bushing
24, 24' bow arms
25 arch
26 fixture/ring
27 Hall effect sensor
28 cable
29 support ring
30, 30' stretching rod
31, 31' retention clip
32, 32' hollow cylinder
33 thread
34 connection element
35, 35' lid
36, 36' connection web
37, 37' proximal rod portion
38, 38' distal rod portion
39 threaded screw
40 compression spring
41 threaded pin
42 end portion
43 head of the threaded screw 39
44 lid
45 head of the threaded screw 17
46 cylindrical sleeve
47 cylindrical coil
48 bore

The invention claimed is:

1. A device comprising a fastening device of a penis extension device, a coupling element for exerting a tensile force on a penis, and a tensile force meter, wherein
    a first electronics component and a first current source are present;
    the tensile force meter electrically or electronically determines a measurement value for an exerted tension together with the first electronics component; and
    the first electronics component has a first radio device for transmitting the measurement value to an external receiver.

2. The device as claimed in claim 1, wherein the tensile force meter comprises a strain gauge or a distance measurement device.

3. The device as claimed in claim 2, wherein the distance measurement device is an inductive, resistive or capacitive distance measurement device.

4. The device as claimed in claim 3, wherein the distance measurement device comprises a Hall effect sensor.

5. The device as claimed in claim 1, wherein the first radio device is a Bluetooth device.

6. The device as claimed in claim 1, wherein the tensile force meter, the first electronics component and the first current source are integrated in the coupling element.

7. The device as claimed in claim 1, wherein the coupling element is an element which is separate from the fastening device and which is suitable for being connected to the fastening device, but also for being released form the latter again.

8. The device as claimed in claim 1, wherein the fastening device has an elongate, rigid hollow body which is open at the proximal end and which is suitable for receiving the distal end of the penis and for fastening to the penis extension device and has an opening which is operatively connected to a vacuum pump or can be brought into such operative connection, and wherein the fastening device is suitable for being connected to a penis by means of an elastic tubular sleeve, wherein the sleeve is suitable for bearing with its proximal area on the shaft of the penis and, in the assembled state of the fastening device, for having its distal area enclosing the proximal end of the hollow body and bearing on the outside thereof, wherein a pressure meter is present for determining the pressure prevailing inside the hollow body, and either (i) the pressure meter electrically or electronically determines the pressure measurement value together with the first electronics component, and the first radio device of the first electronics component is suitable for transmitting the determined pressure measurement value to an external receiver, or (ii) a second electronics component and a second current source are present, the pressure meter electrically or electronically determines the measurement value for the pressure together with the second electronics component, and the second electronics component has a second radio device for transmitting the determined measurement value to an external receiver.

9. A device comprising a fastening device of a penis extension device, a coupling element for exerting a tensile force on a penis, and an elastic tubular sleeve, wherein the fastening device has an elongate, rigid hollow body which is open at the proximal end and which is suitable for receiving the distal end of the penis and for fastening to the penis extension device and has an opening which is operatively connected to a vacuum pump or is suitable for being brought into such operative connection, and wherein the fastening device is suitable for being connected to a penis by means of the elastic tubular sleeve, wherein the sleeve is suitable for bearing with its proximal area on the shaft of the penis and, in the assembled state of the fastening device, for having its distal area enclosing the proximal end of the hollow body and bearing on the outside thereof, wherein a pressure meter is present for determining the pressure prevailing inside the hollow body, the pressure meter electrically or electronically determines the pressure measurement value together with a first electronics component, and the first electronics component has a first radio device for transmitting the determined pressure measurement value to an external receiver.

10. The device as claimed in claim 9, wherein a three-way valve is arranged between the opening and the vacuum pump and can adopt the following settings:

(i) the interior of the hollow body is connected to the environment, (ii) the opening and therefore the hollow body are closed, and (iii) the interior of the hollow body is connected to the vacuum pump.

11. The device as claimed in claim 10, wherein the three-way valve has a rotatable sealing disk in which at least one continuous opening is provided, which continuous opening is arranged off-center and can be brought into alignment with the opening by rotation of the sealing disk, and a further continuous opening is provided in the sealing disk, which further continuous opening is likewise arranged off-center and can be brought into axial alignment with the opening by rotation of the sealing disk and communicates with the environment via a channel, and the sealing disk can be rotated in such a way that the opening is closed.

12. The device as claimed in claim 9, wherein the fastening device is integrated together with the coupling element in a penis extension device.

13. A device comprising a penis extension device, a fastening device, and a coupling element for transmitting force, wherein:

(i) the penis extension device is equipped with a support ring which is suitable for supporting on the body of the user, and with two longitudinally adjusted stretching rods which are articulated in parallel on the support ring and are axially resiliently mounted and (ii) the coupling element is arranged at the distal end of the two stretching rods and is suitable for connecting the fastening device to the two stretching rods and for exerting a tensile force on a penis, wherein a first electronics component and a first current source are present, the tensile force meter electrically or electronically determines a measurement value for the exerted tension together with the first electronics component, and the first electronics component has a first radio device for transmitting the measurement value to an external receiver, and the first electronics component, the first current source and the tensile force meter are arranged in one of the two stretching rods, in both stretching rods or in the coupling element.

14. The device as claimed in claim 13, wherein the coupling element is suitable for being connected to the two stretching rods, but also for being released form the latter again.

15. A coupling element for a penis extension device, which is suitable for transmitting a tensile force to a fastening device for a penis, wherein the coupling element is an element separate from the fastening device and is suitable for being connected to the fastening device, and also for being released from the latter again, said coupling element comprising a first electronics component, a first current source and a tensile force meter, which electrically or electronically determines a measurement value for an exerted tension, are integrated in the coupling element, and the first electronics component has a radio device for transmitting the measurement value to an external receiver.

* * * * *